United States Patent [19]
Ashby

[11] Patent Number: 5,454,816
[45] Date of Patent: Oct. 3, 1995

[54] FEMORAL CUTTING GUIDE

[75] Inventor: Alan M. Ashby, Maidenhead, England

[73] Assignee: Howmedica International Inc., Shannon County Clare, Ireland

[21] Appl. No.: 248,829

[22] Filed: May 25, 1994

Related U.S. Application Data

[63] Continuation of Ser. No. 7,931, Jan. 25, 1993, abandoned.

[30] Foreign Application Priority Data

Feb. 7, 1992 [GB] United Kingdom ................... 9202561

[51] Int. Cl.[6] ................................................. A61B 5/103
[52] U.S. Cl. ................... 606/88; 606/96; 606/102
[58] Field of Search ........................ 606/88, 87, 96, 606/102, 86, 82, 79, 80; 623/20

[56] References Cited

U.S. PATENT DOCUMENTS

| | | |
|---|---|---|
| 4,457,307 | 7/1984 | Stillwell . |
| 4,474,177 | 10/1984 | Whiteside . |
| 4,487,203 | 12/1984 | Androphy . |
| 4,502,483 | 3/1985 | Lacey . |
| 4,524,766 | 6/1985 | Petersen . |
| 4,567,885 | 2/1986 | Androphy . |
| 4,653,488 | 3/1987 | Kenna et al. ............................ 606/88 |
| 4,718,413 | 1/1988 | Johnson . |
| 4,892,093 | 1/1990 | Zarnowski . |
| 4,926,847 | 5/1990 | Luckman ................................. 606/88 |
| 5,053,037 | 10/1991 | Lackey ..................................... 606/79 |
| 5,122,144 | 6/1992 | Bert et al. ................................ 606/88 |
| 5,129,909 | 7/1992 | Sutherland ............................... 606/88 |

FOREIGN PATENT DOCUMENTS

| | | |
|---|---|---|
| 0243109 | 10/1987 | European Pat. Off. . |
| 0340176 | 11/1989 | European Pat. Off. . |
| 0378294 | 7/1990 | European Pat. Off. . |
| 380451 | 8/1990 | European Pat. Off. ................. 606/88 |
| 0466659 | 1/1992 | European Pat. Off. . |
| 2664157 | 1/1992 | France . |

Primary Examiner—Stephen C. Pellegrino
Assistant Examiner—Guy V. Tucker
Attorney, Agent, or Firm—Peter C. Richardson; Lawrence C. Akers; Raymond W. Augustin

[57] ABSTRACT

An orthopedic instrument for guiding a saw blade for preparing the distal end of a human femur to receive an endoprosthetic femoral component has a base component provided with guide for guiding cutting blades. The guide can be used to shape all of the necessary femoral surfaces to receive the femoral component to be fitted once the base component is fitted to the bone. A device for aligning the base component on the bone elements for attaching the base component to the bone after alignment is also provided.

14 Claims, 16 Drawing Sheets

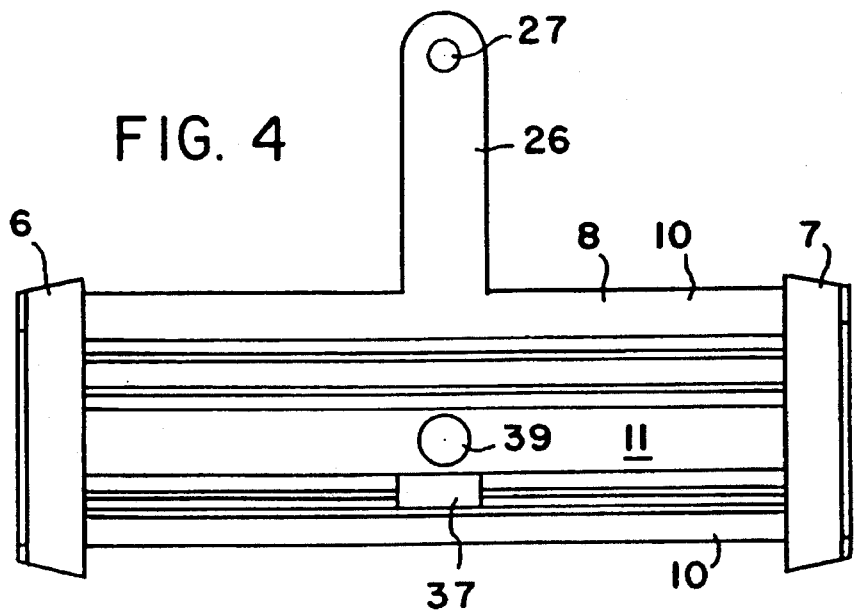
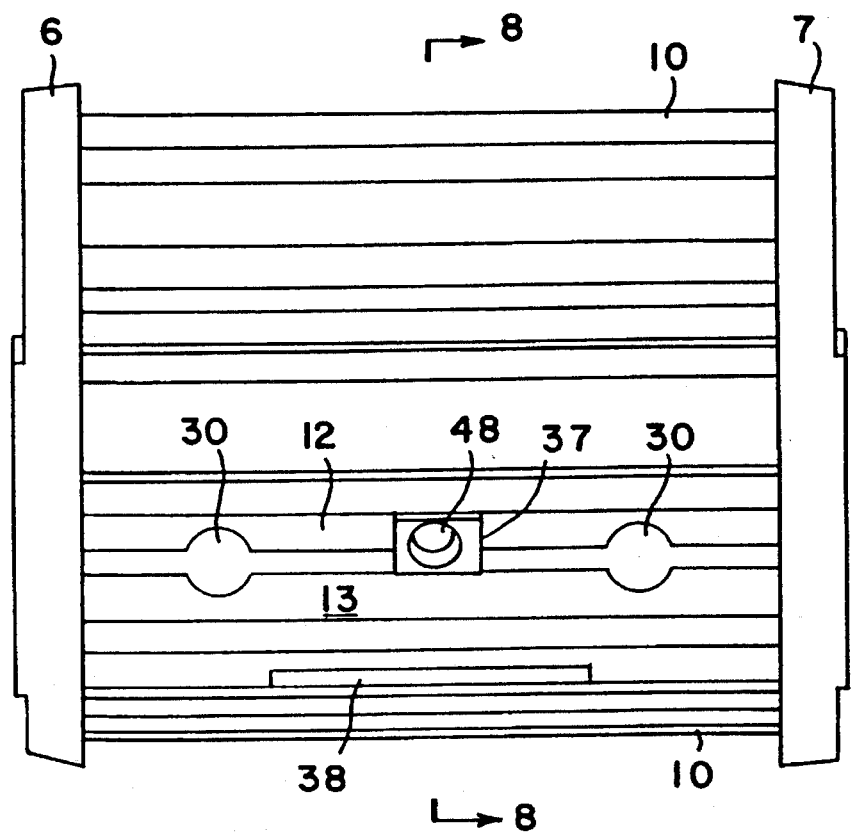

FEMORAL CUTTING GUIDE

This is a continuation of application Ser. No. 08/007,931, filed on Jan. 25, 1993, now abandoned.

BACKGROUND OF THE INVENTION

1. Field of the Invention

This invention relates to an orthopedic instrument for guiding a saw blade for shaping the distal end of a human femur to receive an endoprosthetic femoral component.

2. Description of the Prior Art

Instruments used to prepare bone surfaces and to place femoral endoprosthetic components in the knees perform two basic functions.

First is the control of power and other tools to provide accurate fixation surfaces of bone that match implant geometry. Second is to position fixation surfaces relative to bone and soft tissue architecture to appropriately orient the prosthetic component.

In addition, instruments must provide the necessary flexibility to accommodate the variations in geometry and surgical complications that are encountered within the patient population. They must also meet the disparate needs of surgeons who wish to follow different methodologies when performing the surgical replacement of the knee.

Conventional femoral components usually have five planar fixation surfaces which match the bone to the implant. Thus the femur must be prepared to have a distal cut surface, a posterior cut surface, an anterior cut surface, an anterior chamfer cut surface and a posterior chamfer cut surface.

Some existing femoral components have marginally different forms of fixation surface, ie. no posterior chamfer, or the anterior chamfer surface formed as a curved surface rather than a flat one. In general it has been found that flat surfaces are nevertheless advantageous since they are easier to prepare using oscillating saws.

A number of different surfaces can be used to control the positioning of the essentially planar blades of front or side cutting oscillating saws for shaping the planar surfaces.

Flat metallic blocks on which the saw blade is rested, obviously rely to some extent on the skill of the surgeon to avoid tilting of the saw blade, as may happen when the saw encounters a localized harder section of bone, or when the saw blade has a long travel beyond the guide surface.

Slots having small clearance relative to the thickness of the saw blade may also be used. In general these offer better control of the saw blade than blocks, but they can impede visibility at the operative site. Simple slots do not provide clearance for the tooth set on the saw blade, but a number of solutions have been proposed to this problem. These include variable thickness slots formed by assemblies of elements.

The slot is temporarily made deeper to allow passage of the saw blade teeth and subsequently reduced to more closely hold the main body of the blade in position. Alternatively, the slot is made open ended on one side so that the blade may be introduced into it from the side without having to pass the teeth through the slot. Variations in the design of the saw blade itself have also been used. These may have zero net set on the teeth or provide a local clearance behind the teeth so that the total blade and tooth form can be passed through a close clearance slot.

Block type cutting guides are shown in U.S. Pat. Nos. 4,474,177, 4,487,203, 4,502,483, 4,524,766 and 4,567,885.

Fulcrum type cutting guides are described in U.S. Pat. No. 4,718,413 and also in U.S. Pat. No. 4,892,093. These consist of an upper and a lower guide surface which are linearly separated along the plane of intended cut by the saw blade. By providing a separation between the two surfaces the saw blade, including its tooth set, may be introduced between the two surfaces and then biased against them to control the cutting plane. The separation of the guide surfaces normal to the plane of operation of the saw blade is matched to the thickness of the saw blade. The choice of orientation of the guide surfaces is chosen so that any deviation by the surgeon in maintenance of the contact between the saw blades and either of the guide surfaces results in conservative removal of bone, which may be corrected subsequently. The guide of U.S. Pat. No. 4,892,093 sits on the already prepared distal femur and provides for the cutting of four additional cuts.

The femoral components may be located with six degrees of freedom relative to the patients femoral geometry. These can be expressed in a cartesian manner relative to orthogonal anatomical reference planes.

Angulation:
  Varus-Valgus,
  Flexion-Extension,
  Internal-External Rotation.

Linear Position:
  Inferior-Superior,
  Anterior-Posterior,
  Medial-Lateral.

To position the component on the bone, a number of datum features of the patients anatomy and their relative location as controlled by soft tissue structures at the knee may be utilized.

Two major schools of though exist as to the optimum method to provide consistent functional placement. The first is independent femoral anatomical placement. In this method the femoral component is positioned on the femur by referencing datum features on the femur itself.

The second is referenced to the tibial position. In this method the position of the femoral component is controlled relative to the proximal cut of the tibia. The ligaments and other soft tissue structures at the knee joint will in this case affect the femoral components position. The positional referencing, according to different methodologies, is performed surgically prior to placing the femoral component.

A third method is varus-valgus and flexion-extension. Angulation of the component in planes is usually performed simultaneously. The reference datum is either the femoral shaft or the line joining the center of the knee and the hip joints. Two major methods for accomplishing this are currently used.

First is intramedullary alignment. A rod is introduced through the center of the knee into the intramedullary space and passed up the inside of the femur to the internal isthmus, picking the axis of the femoral shaft. This technique has been found to be very reliable, but is thought by some surgeons to be overly invasive and in patients where there is excessive bowing of the femoral shaft, or where the intramedullary space is blocked, for example by a long stemmed hip implant, it may not be available.

The second is extramedullary alignment. An external guide rod is aligned with the anterior cortex of the femur, or from the center of the knee to the femoral head.

The posterior condyles of the femur are used in the anatomical approach. In the referenced technique the internal-external rotation is controlled by balancing of the flexion gap so that the medial and lateral compartments of the joint are equally spaced or tensed.

Inferior-Superior positioning is controlled in the anatomical approach by a fixed amount of bone being resected from the distal femur. The amount of resection is normally the same as the thickness of the distal portion of the implant component where bone stock has not been eroded away. In the referenced technique the amount of bone to be removed is adjusted relative to the proximal tibial cut to allow for the total thickness of both the femoral and tibial components.

In the anatomical approach the anterior-posterior position of the femoral component may be referenced to a number of alternative features at the distal femur. These include the posterior condyles, where an amount of bone is resected from the posterior condyles which corresponds either to the posterior thickness of the femoral component or to some proportion or fixed amount in excess of this. Alternatively, anterior features or the distal femur may act as references, usually either the anterior cortex or the deepest point of the patella groove. In cases where a large intramedullary stem is to be used, the position of the femoral component may need to be chosen to match the position of the implant stem within the intramedullary canal in which it must fit. In the referenced approach a posterior resection of the femur is performed so that the flexion gap of the joint matches the thickness of the femoral and tibial components. In general all these approaches result in either an anterior or posterior cut being performed. Subsequently the opposite cut is performed so that the implant will fit between these resected surfaces.

The medial-lateral placement of the component is usually performed by eye to match the rim geometry of the resected bone surface performed by all the previous cuts. In cases where a large intramedullary stem is used, the position may be dictated by the fit of the stem into the intramedullary cavity.

Current techniques generally require the sequential use of alignment and cutting guides. In all current systems multiple cutting guides are needed to fully prepare the distal femur for the implant. Because these sequential operations require the assembly and disassembly of instrument configurations and the use of intermediate datums cut onto the bone, there are penalties in terms of time of operation and accuracy. The current invention is intended to address these inadequacies while incorporating the flexibility to allow for alternative operative approaches to be used in placement of the femoral component.

SUMMARY OF THE INVENTION

According to the present invention an orthopedic instrument for guiding means for shaping the distal end of a human femur to receive an endoprosthetic femoral component is characterized by a base component provided with a guide for guiding cutting elements for shaping all of the necessary surfaces to receive the femoral component to be fitted once said base component is fitted to the bone. Also included are alignment elements for aligning the base component on the bone and elements for attaching the base component to the bone after alignment. Preferably the guide includes guide elements for guiding a saw blade.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 4 is a front elevation of the base component shown in FIG. 3;

FIG. 5 is a plan view of the component as shown in FIG. 3;

DESCRIPTION OF THE PREFERRED EMBODIMENT

Figure 1:
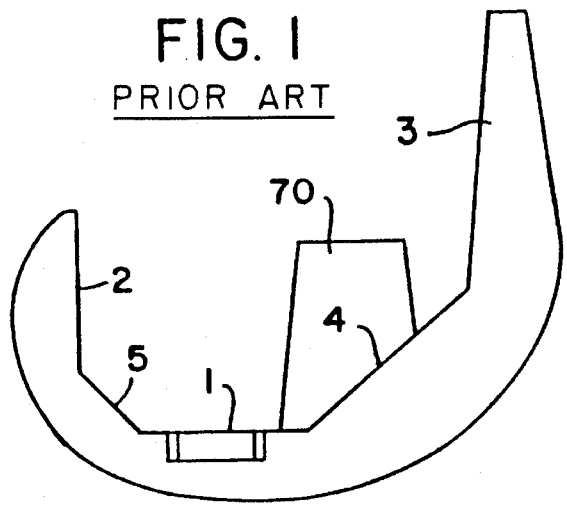
FIG. 1 is a side elevation of a conventional femoral component.

FIG. 1 is a side elevation of a conventional femoral component having five planar fixation surfaces which match the bone to the implant. Reference numeral 1 indicates the distal cut surface, reference numeral 2 the posterior cut surface, reference numeral 3 the anterior cut surface, reference number 4 the anterior chamfer cut surface and reference numeral 5 the posterior chamfer cut surface.

Figure 2:
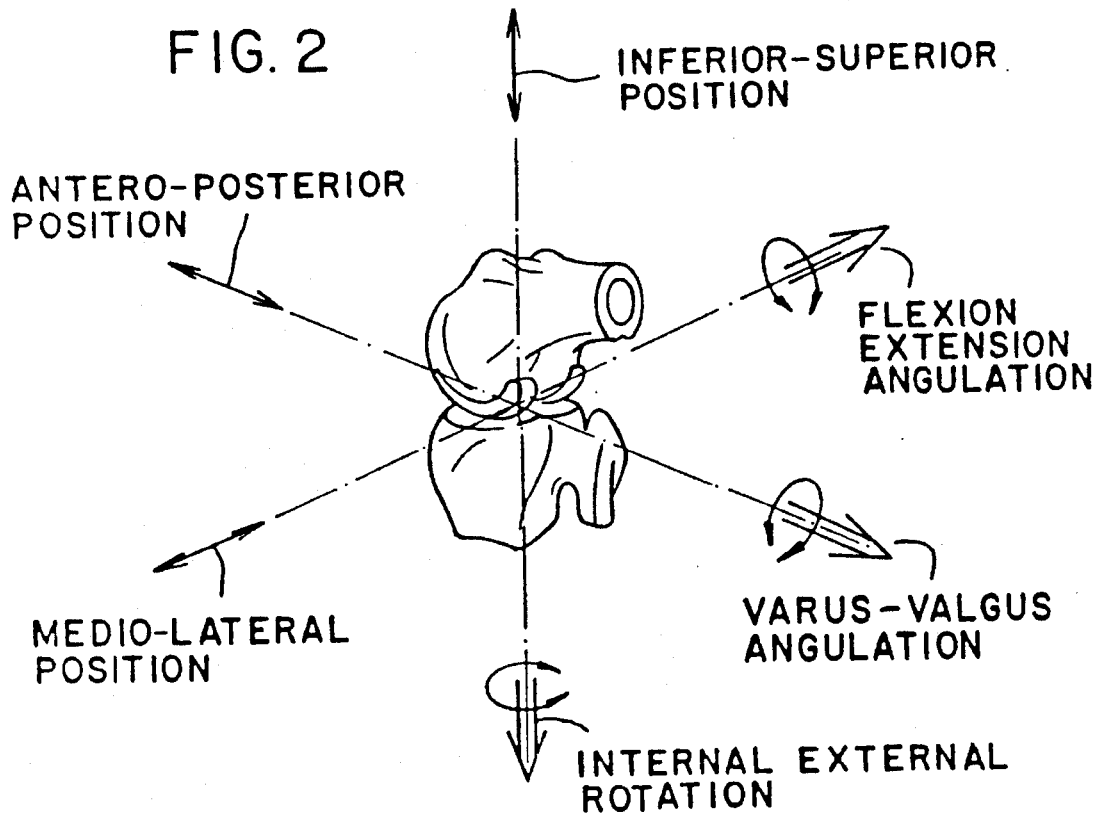
FIG. 2 is a diagram showing the various reference directions for a knee.
Figure 3:
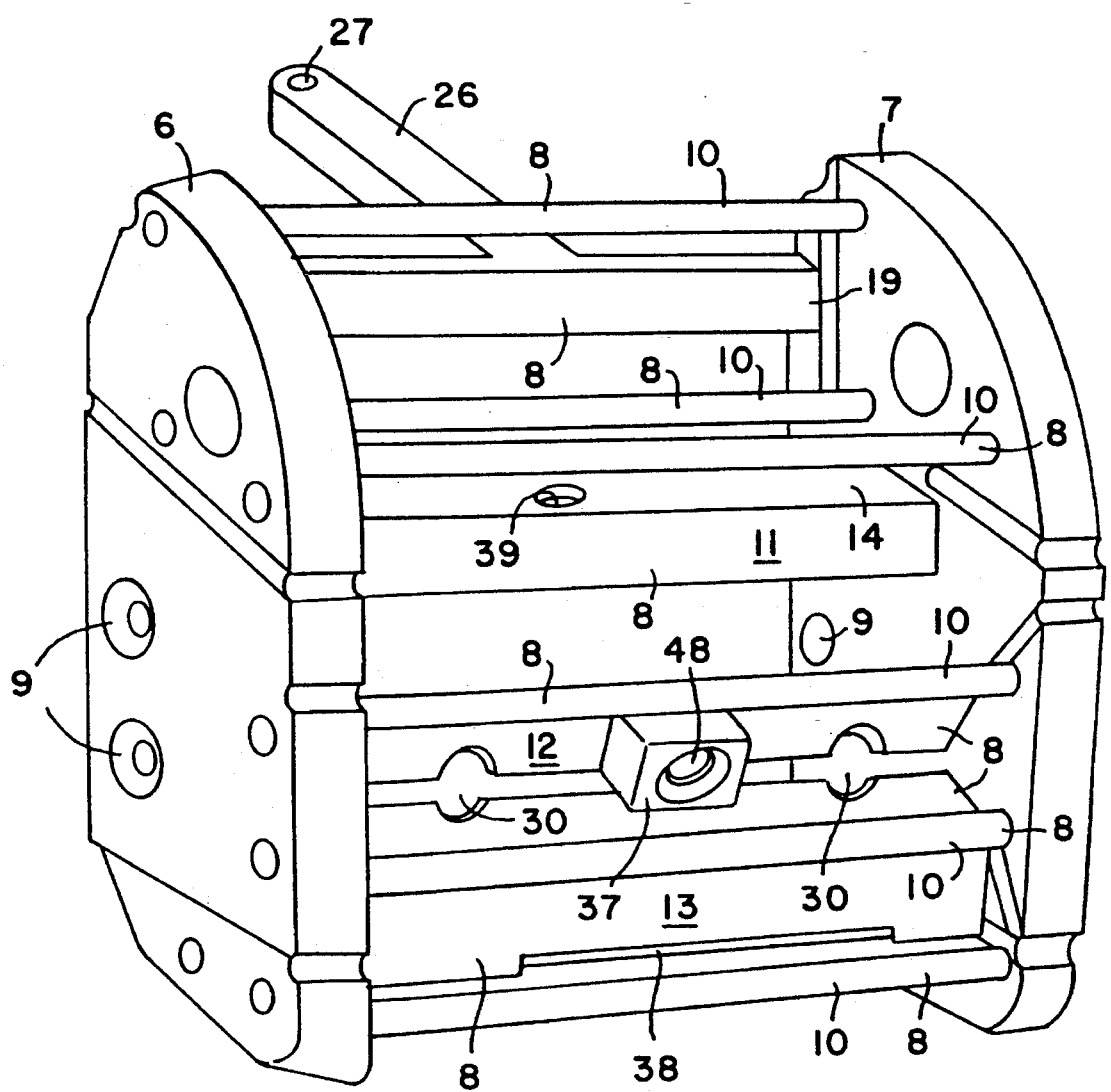
FIG. 3 is an isometric view of a base component of the orthopedic instrument according to the present invention.
Figure 7:
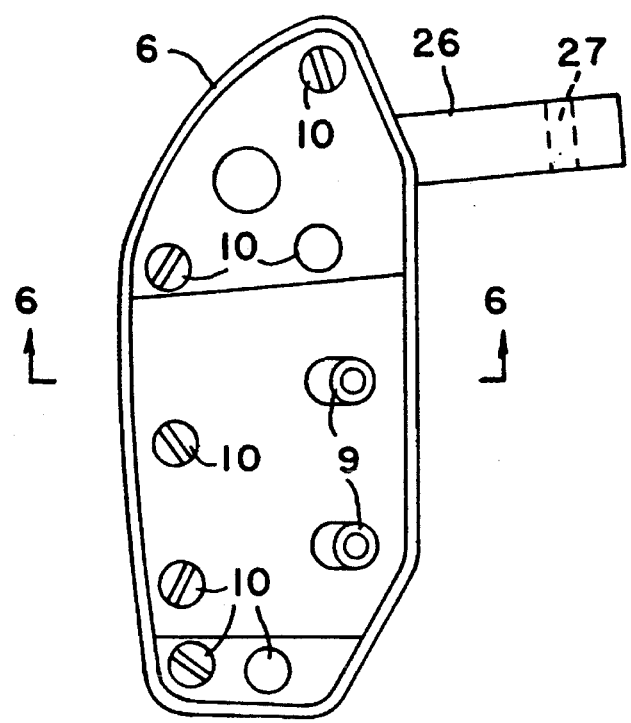
FIG. 7 is an end view of the component as shown in FIG. 3.
Figure 6:
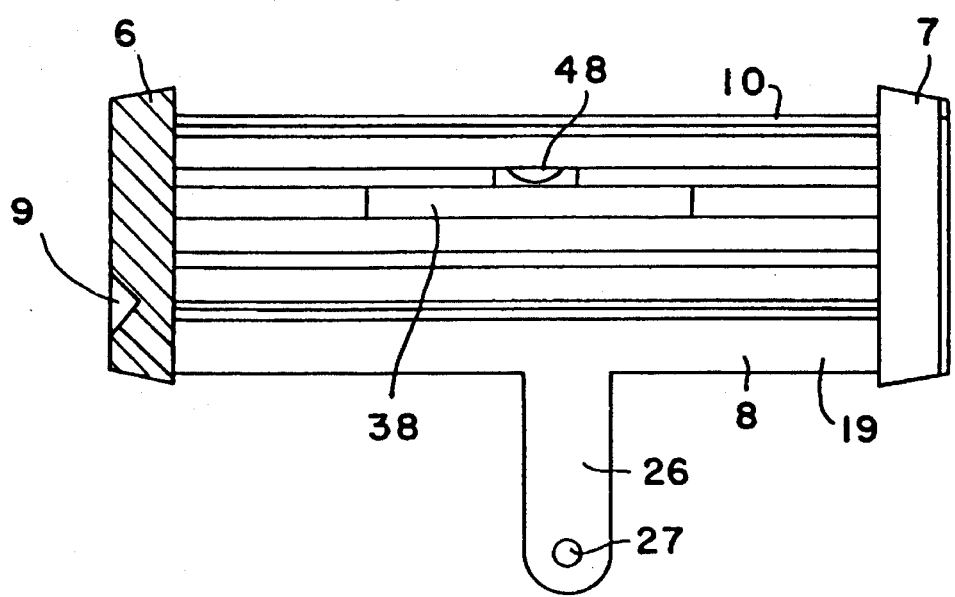
FIG. 6 is a partial cross-sectional rear elevation of the component as shown in FIG. 3 with the partial cross-sectional portion taken on the line 6—6 of FIG. 7.

The femoral component can be located with six degrees of freedom, relative to the patients femoral geometry and FIG. 2 shows the various reference directions for a patients knee. The various degrees of freedom can be expressed in a cartesian manner relative to orthogonal anatomical reference planes as follows:

Angulation: Varus-Valgus, Flexion-Extension,

Internal-External Rotation.

The Linear Position: Inferior-Superior,

Anterior-Posterior and Medial-Lateral.

The preferred embodiment of the orthopedic instrument of the present invention comprises a base component which is used with various accessories. The base component, as shown in FIGS. 3–8, comprises two side plates 6, 7 joined by a number of parallel guide members 8. These structures are used to control the positioning of an oscillating saw blade so that it matches the shape of the femoral component to be implanted. The geometry of guide members 8 allows for the cutting of all five cuts to place a femoral component without any repositioning of the base component relative to the bone.

Each side plate 6, 7 has a pair of angled through holes 9 such that four elongated pins (not shown) can be used to position the instrument in place on the distal femur. The positioning of these is such that the pins pass into bone that will not be removed from the femur during preparation for the implant. The parallel guide members 8 joining the side plates 6, 7 are either manufactured integrally with them, for example by casting or machining, fabricated by welding or assembled, for example by screwing and dowelling.

Seven of the parallel guide members 8 are shown in this embodiment as part threaded headed rods 10 which are screwed across from on plate 6 to the other 7. This allows for the use of alternative diameter rods to accommodate differing thicknesses of saw blade as sold by various manufacturers. Differing thicknesses of saw blade may also be used for each of the cuts. A thin short blade may be most appropriate to the access and cutting of the posterior and posterior chamfer surface, where the required travel of the saw blade is short and longer blades may result in less accurate cuts due to excessive movement at the cutting teeth. When cutting the anterior and distal cuts, a longer and thicker blade may be needed to give the required cut length and stiffness of blade to avoid deviation when harder sections of bone are encountered. In addition, the use of separable rod structures allows them to be manufactured from harder materials, or to be coated in some way to minimize wear and the generation of metallic debris due to the rubbing action of the saw blade.

The size of the guide members is kept as small as possible to maximize the visibility of the bone through the cutting frame, consistent with providing enough control of the saw blade. The other three guide members 8 are provided by cross bars 11, 12 and 13, 19 which have guide surfaces 14, 15, 16, 17, 18 and 25 respectively.

Figure 8:
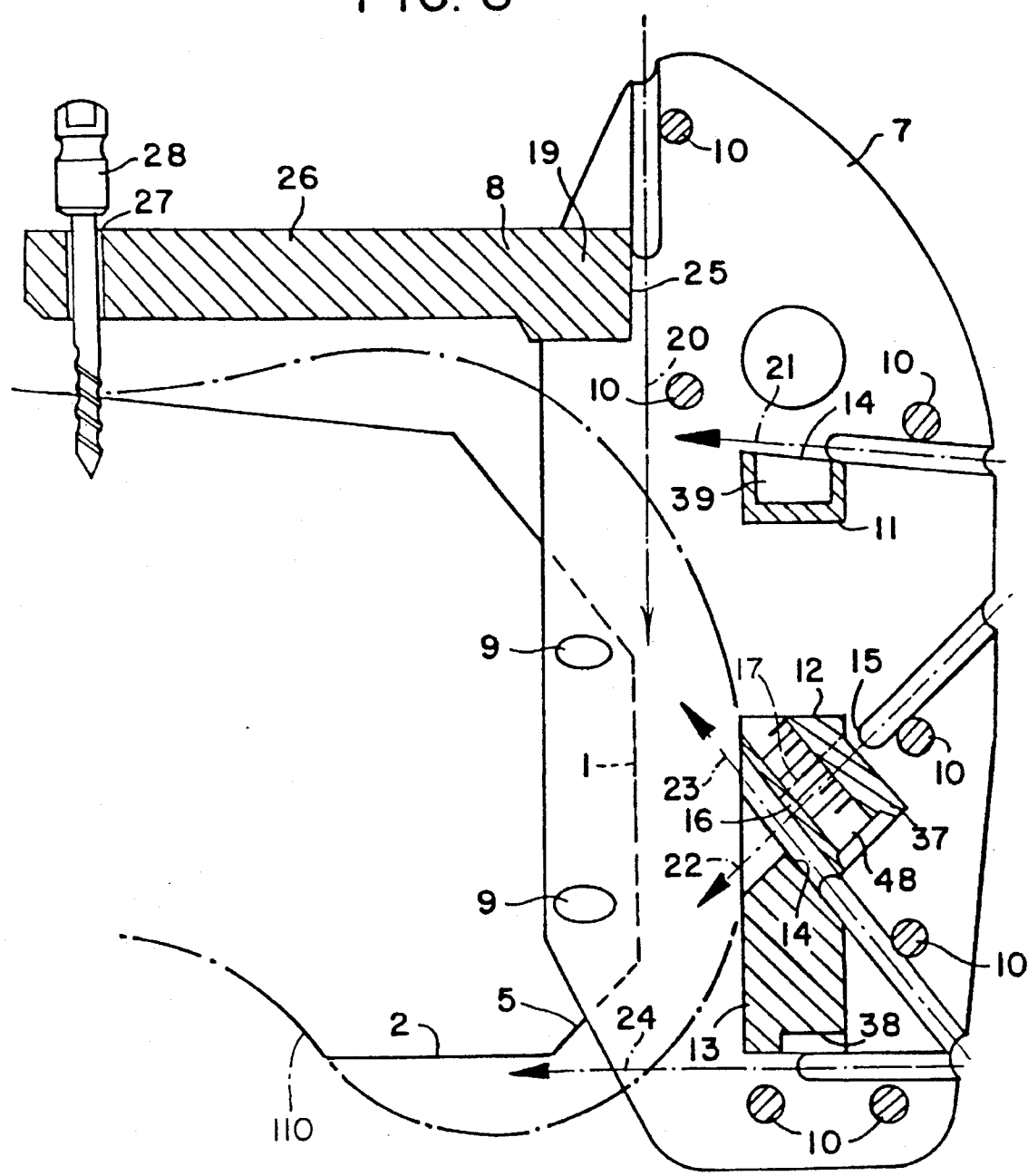
FIG. 8 is a cross-sectional view taken on the line 8—8 of FIG. 5.
Figure 9:
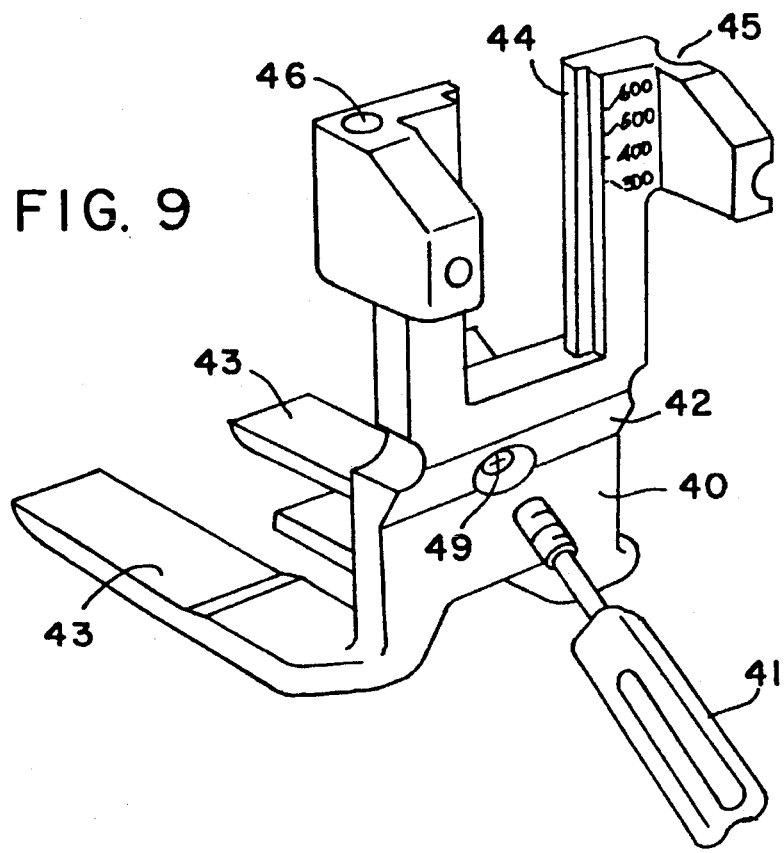
FIG. 9 is an isometric view of a posterior condylar alignment accessory for use with the base component.
Figure 10:
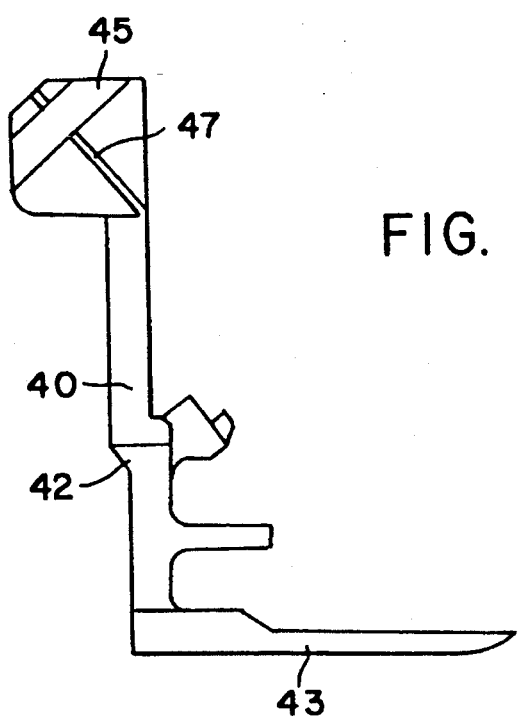
FIG. 10 is a side elevation of the accessories shown in FIG. 9.
Figure 11:
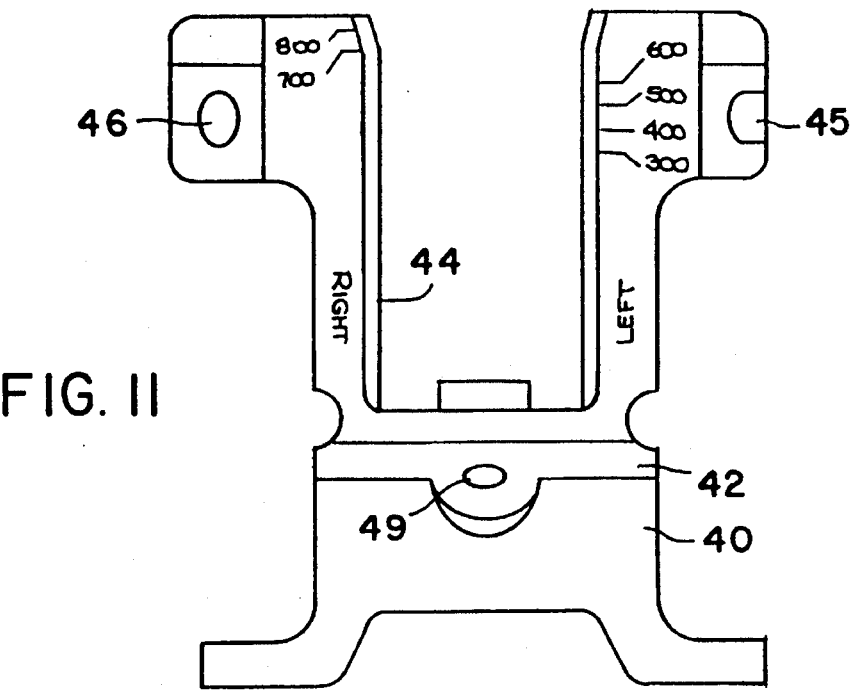
FIG. 11 is an end view of the accessories as shown in FIG. 9.
Figure 12:
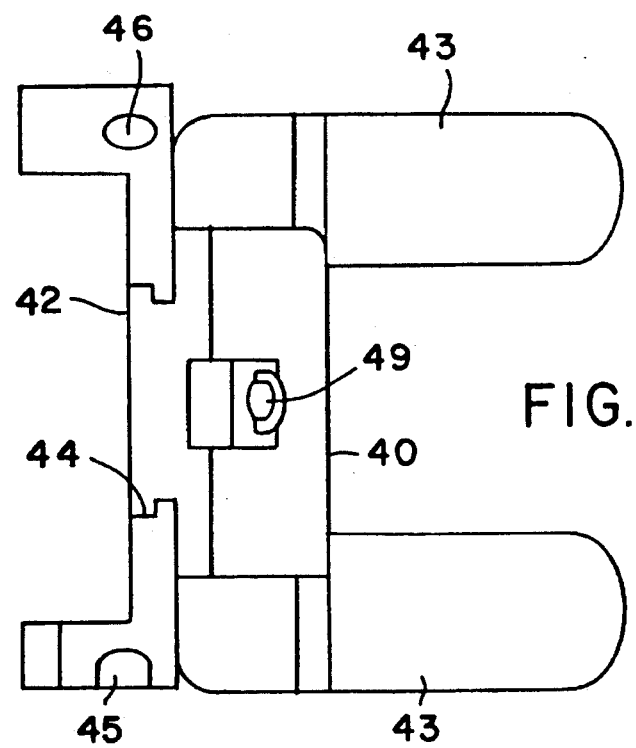
FIG. 12 is a plan view of the accessories as shown in FIG. 9.

The directions of cut between the guide surfaces form five different cuts which are indicated by arrows 20, 21, 22, 23 and 24 in FIG. 8. This figure shows how the base component is located on a femur to be prepared. The shape of the original femur is indicated by broken line 110 and the shaped surfaces to align with the surfaces 1, 2, 3, 4 and 5 shown in FIG. 1 carrying the same reference numerals.

Figure 17:
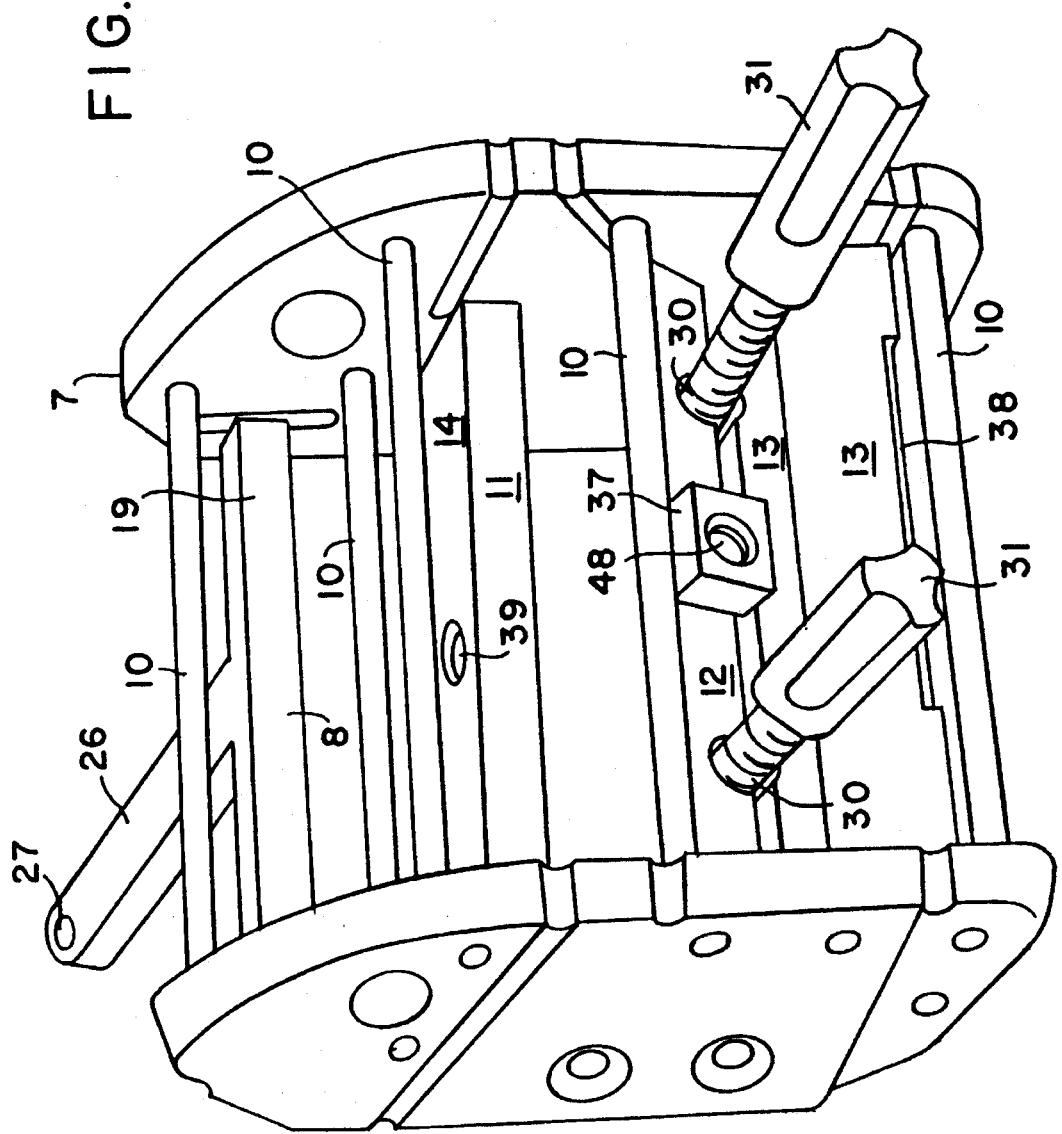
FIG. 17 is an isometric view of the base component provided with condylar defect screws.

Between the two guide surfaces 16, 17 used for the anterior and posterior chamfer there are portions of two halves of a female screw threaded hole 30. These allow threaded bolts 31 to be inserted to stabilize the base component against the distal femur when bone loss is present due to degenerative changes as shown in FIG. 17.

A male boss feature 37 is provided on the cross bar 12. This and a ledge portion 38 on the cross bar 13 form means of attaching a number of accessories. A counterbore 39 is provided on cross bar 11. This allows accessories which are used across a range of guide sizes to be appropriately positioned relative to the intramedullary stem on the femoral component for any of the base component sizes.

The cross bar 19 carries an extension which provides an anterior anchor 26 and is provided with a drill guide 27. This anterior anchor 26 allows a hole to be drilled into the anterior cortex of the femur to allow a fixation pin 28, shown in FIG. 8, to be inserted, which provides a significantly enhanced stability for the instrument on the bone.

Figure 13:
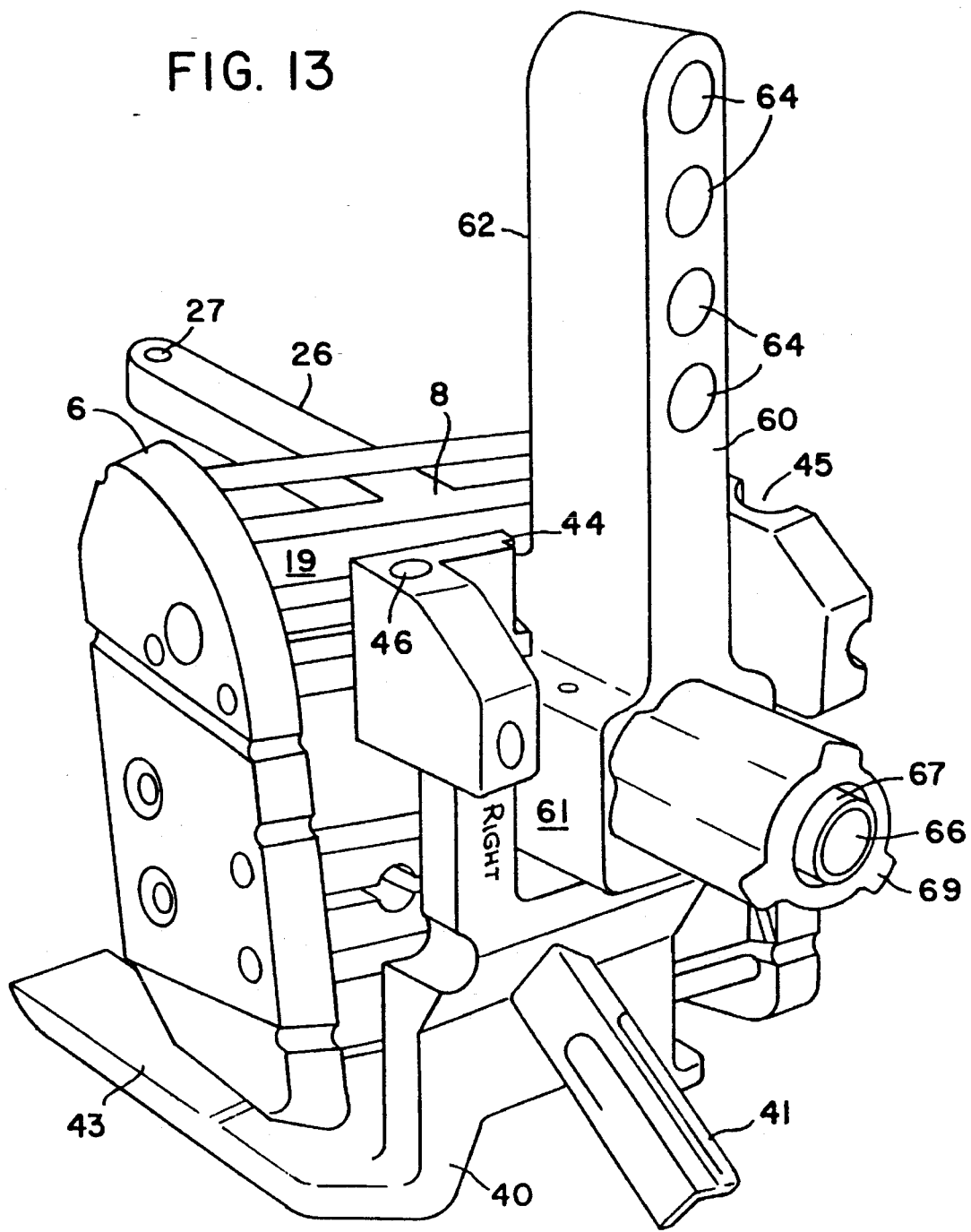
FIG. 13 shows the posterior condylar alignment accessory in position on the base component and carrying an extramedullary alignment and drill guide.

A posterior condylar alignment accessory 40 is shown in FIGS. 9–12, which attaches to the base component using the boss 37 and ledge 38 arrangement via a finger screw 41 as shown in FIG. 13, which screws into a threaded hole 48 in the boss 37 after passing through a hole 49 in a main portion 42, provided with two thin arms 43 which can be located against the posterior condyles. These are made as thin as possible while maintaining enough stiffness and toughness to withstand repeated operative use and act as a condylar sled.

The main portion 42 has a slide 44 which is used as a means of attaching further accessories. This is illustrated in FIG. 13 which shows accessory 40 with its condylar sled and extramedullary alignment guide 60 attached.

Figure 16:
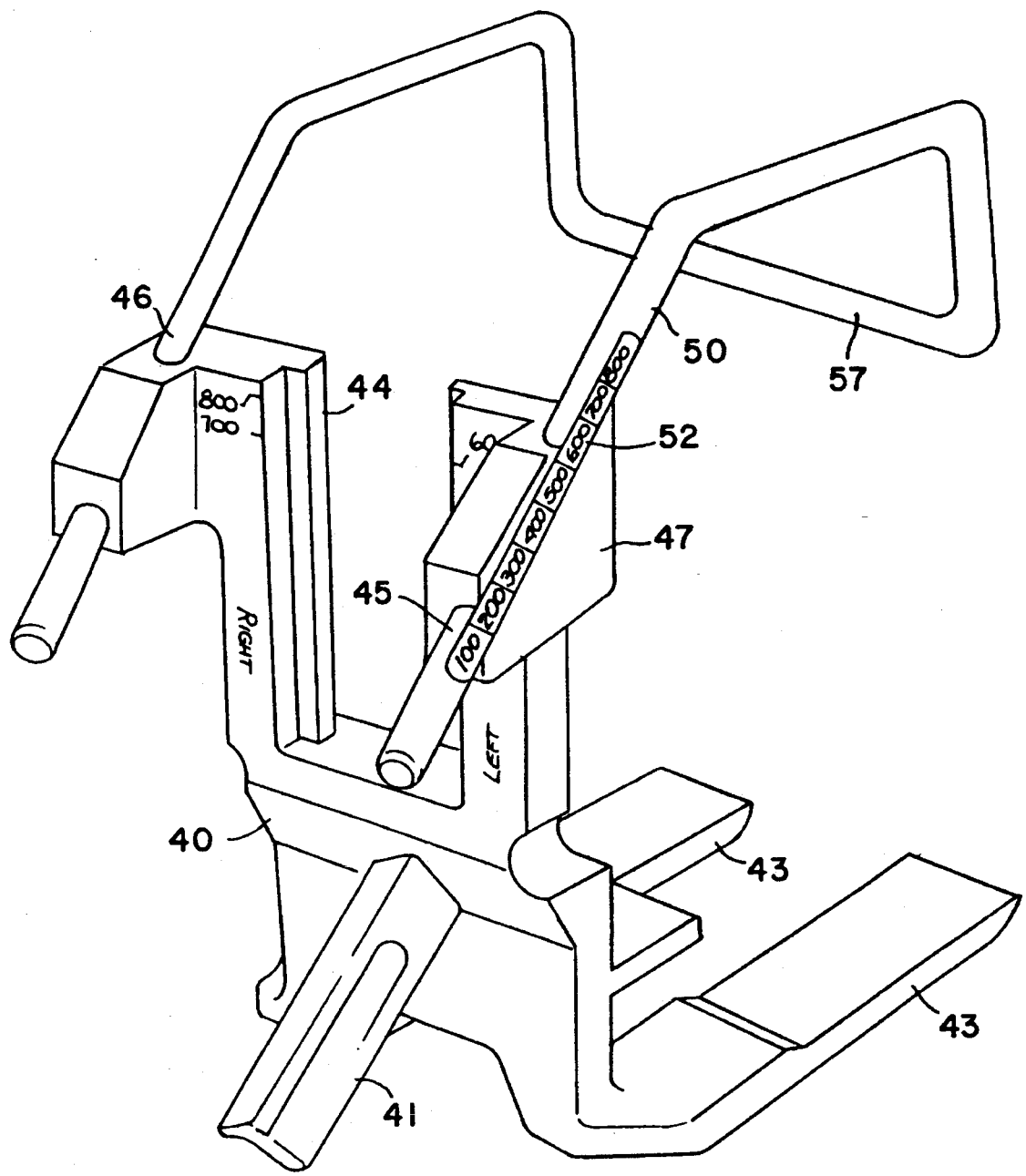
FIG. 16 shows the posterior condylar alignment accessory carrying a sizing stylus.

Anteriorly, accessory 40 has an inclined parallel slot 45 and hole 46 which are used in conjunction with a sizing stylus 50, as shown in FIG. 16. A marker line crosses the slot 45. The angulation of the holes 46 and slot 45 allows a single stylus 50 to be used to check sizing of the base component prior to performing any cuts. Stylus 50 is arranged to move its indicating tip 51 along the locus of the front of the anterior flanges of a range of sizes of femoral component relative to posterior arms 43. When the sizing stylus 50 is pushed up against the anterior cortex of the femur, the appropriate femoral component size is indicated by the position of marker line 47 relative to a scale 52 on the stylus 50.

Figure 14:
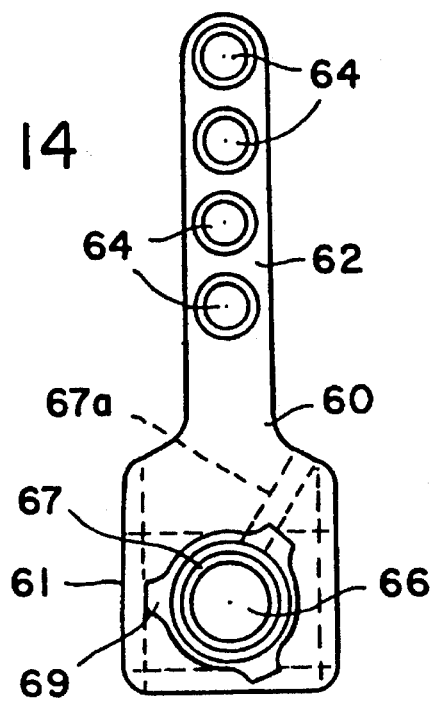
FIG. 14 is a front view of the drill guide as shown in FIG. 13.
Figure 15:
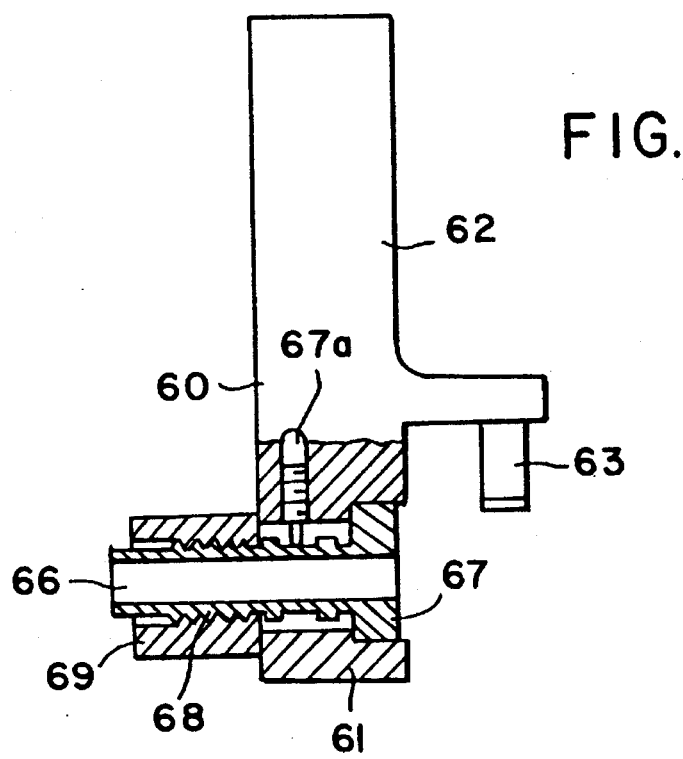
FIG. 15 is an end elevation of the drill guide as shown in FIG. 14 partly in section.

The extramedullary alignment and drill guide 60 depicted in FIG. 13 is shown in FIGS. 14 and 15 and comprises a guide block 61 and extension 62. Guide block 61 is shaped to fit into slide 44 in posterior condylar alignment accessory 40 and a peg 63 engages into counterbore 39 on cross bar 11 as shown in FIG. 15. Guide block 61 is provided with a clamp member 67, one end of which is threaded at 68 to receive a locking hand nut 69. Thus the guide may be securely fastened to posterior accessory 40. A retaining screw 67a engages the clamp member 67 to prevent complete removal thereof when the hand nut 69 is released. Guide 60 may be similarly positioned into the other positioning accessories that fit onto the base component, which have slideways equivalent to slideway 44 on posterior accessory 40.

Figure 21:
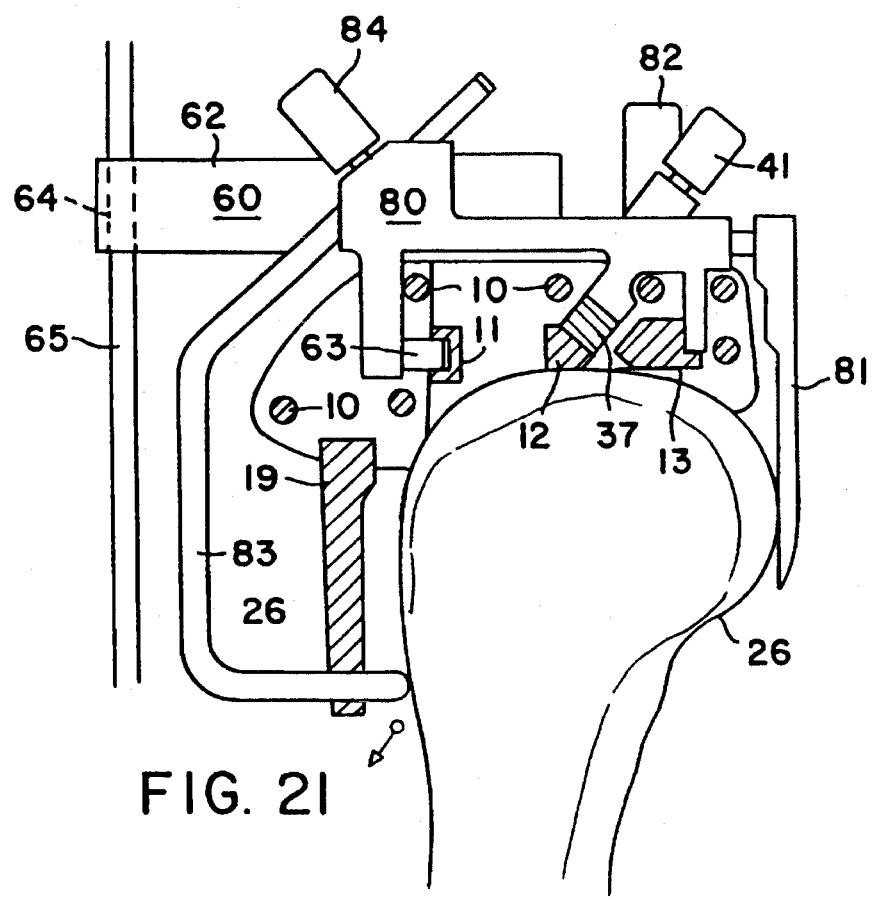
FIG. 21 shows alternative accessories in position on the base component.

A number of parallel through holes 64 in drill guide 60 are used with long alignment rods 65 as shown in FIG. 21 to orient the instrument assembly relative to the femoral geometry. These are positioned to overlie the anterior surface of the femur. Alternative holes are available to allow placement of the guide rods as close to the patient as possible. The preferred technique is to align to the femoral head from the center of the knee for varus-valgus alignment. Flexion-extension alignment is performed by moving the base component until alignment rod 65 is parallel with a line joining the center of the knee and the greater trochanter. Alternative extramedullary alignment methods may use the line of the anterior femoral shaft for varus-valgus orientation. In this case an alternative drill guide (not shown) is used in which holes 64 for the alignment rod are angled to compensate for the valgus angle of the femoral shaft relative to the mechanical axis of the femur, ie. the line between the hip and knee centers.

In the preferred embodiment drill guide 60 also incorporates a drill bushing 66 which extends through clamp member 67. This allows an entry hole to be formed into the intramedullary cavity. The position of this entry hole is controlled so that it corresponds with the position of the intramedullary stem 70 on the femoral implant. In this way a further degree of repeatability of technique is gained, current methods relying on "eyeballing" of this entry hole, and the removal of bone is such that it will not compromise the fixation of the intramedullary feature of the implant in this area. In existing techniques the intramedullary entry hole may siamese with the fixation surface prepared for the implant's intramedullary feature.

As described with regard to FIG. 17, threaded bolts 31 can be provided which act as condylar defect screws. These can be placed in the screw holes 30 of the base component when it is positioned against the distal femur and allow the guide to be repositioned to make allowance for bone loss caused by degenerative changes, or to adjust the varus-valgus orientation of the bone guide.

Figure 18:
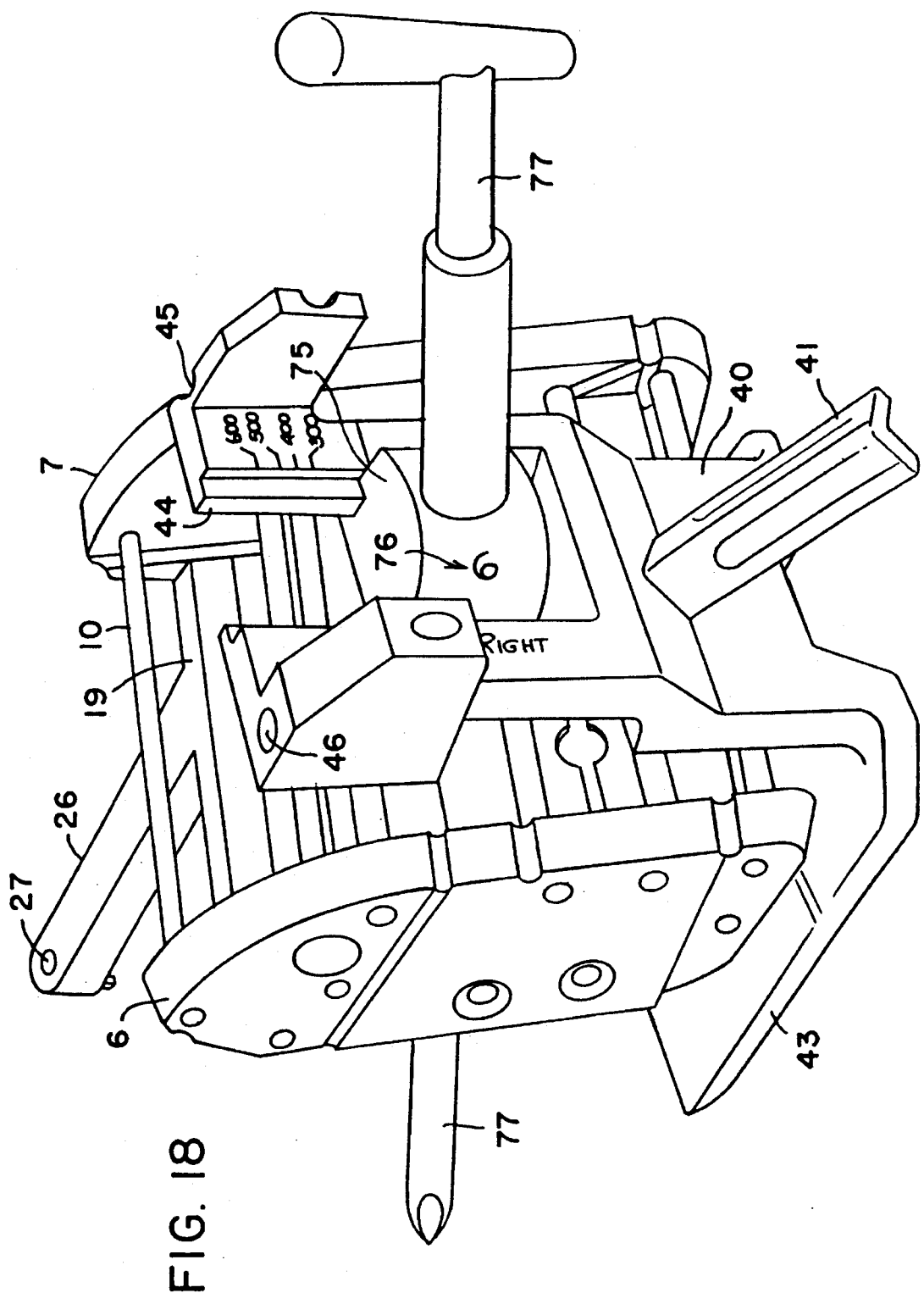
FIG. 18 shows the base component and posterior condylar alignment accessory provided with an intramedullary boss and an intramedullary rod.
Figure 20:
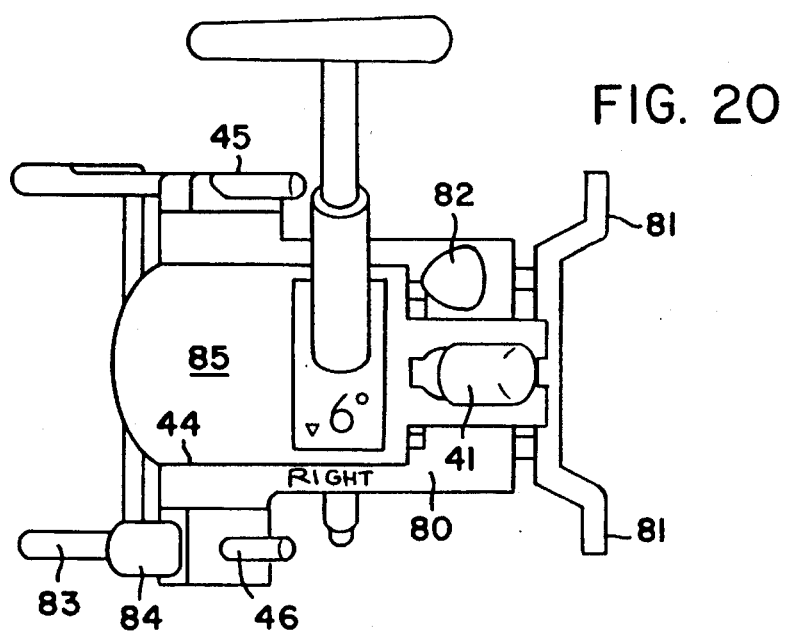
FIG. 20 is a plan view of the accessories in position as shown in FIG. 19.

An intramedullary boss 75 is provided as shown in FIG. 18. The boss 75 fits into the slide 44 on the posterior condylar accessory 40. It also similarly fits in the alternative positioning accessories to be described. The boss 75 is available in a number of different valgus angles as indicated by reference numeral 76, and can be fitted in two opposite senses to suit either right or left limbs. The boss forms a guide for the placement of an intramedullary rod 77 which is passed up into the bone to align the assembly with the femoral canal.

As discussed previously, surgeons may have different preferences in their choice of alignment method and datums. The current system aims to include as much versatility as possible without comprising the ease of performing any one of the approaches when chosen.

There are various alternative femoral alignment methods: Anterior-Posterior Position. The instrument described so far used the posterior condyles to position the femoral component. Alternative instruments for other methods are shown in FIGS. 19, 20, 21 and 22 in which the same reference numerals are used to indicate similar parts to those used in other figures.

Figure 19:
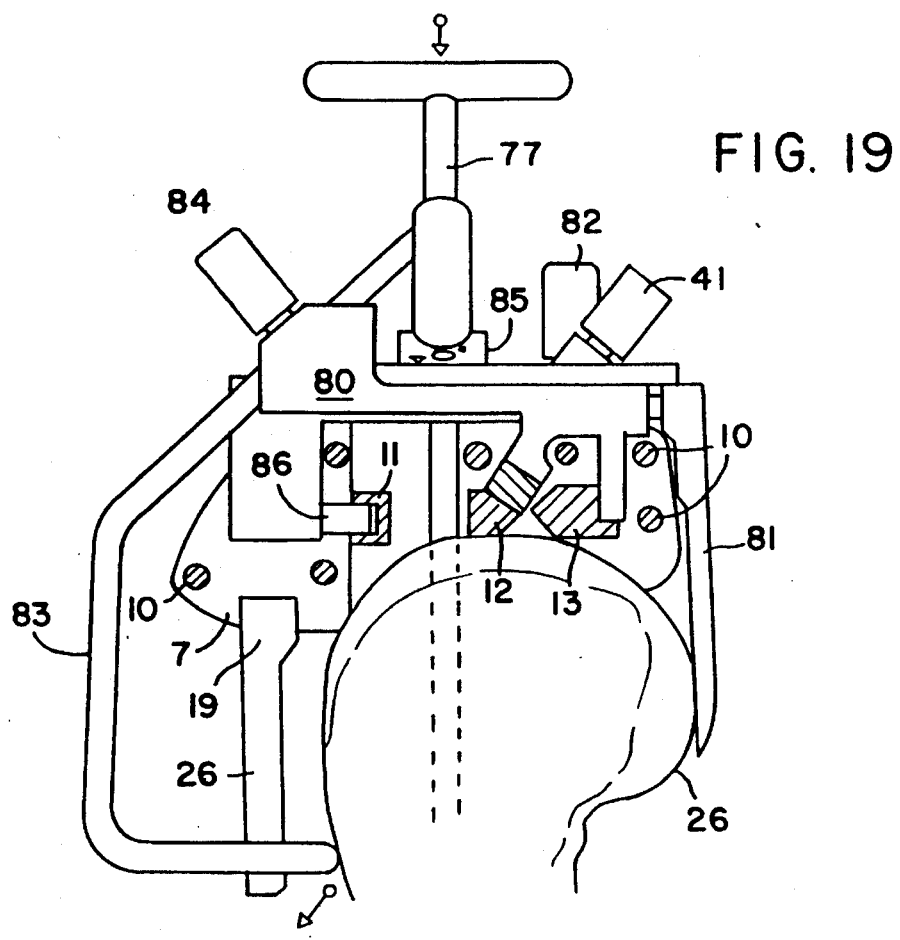
FIG. 19 is a side view of various accessories in position on the base component.

An intramedullary alignment accessory is shown in FIG. 19 which allows the intramedullary rod 77 to be used as the datum for positioning of the femoral component. This is necessary when long intramedullary stems are used. This accessory makes use of an alternative means for locating the extramedullary and pilot drill guide and the intramedullary boss, and consists of a posterior condylar alignment accessory with adjustable condylar sleds. In this construction a device 80 similar to accessory 40 is provided but arms 43 are replaced by a pair of adjustable gauges 81 which can move in relation to main portion 42, and which can be clamped by a screw clamp 82. An alignment gauge 83 similar to sizing stylus 50 can be moved in hole 46 and slot 45 and locked by clamp 84. A further difference is that the boss 75 is replaced by a support member 85, which is located in slide 44 but also has a peg 86 which acts in a similar manner to peg 63 on the drill guide 60.

Figure 22:
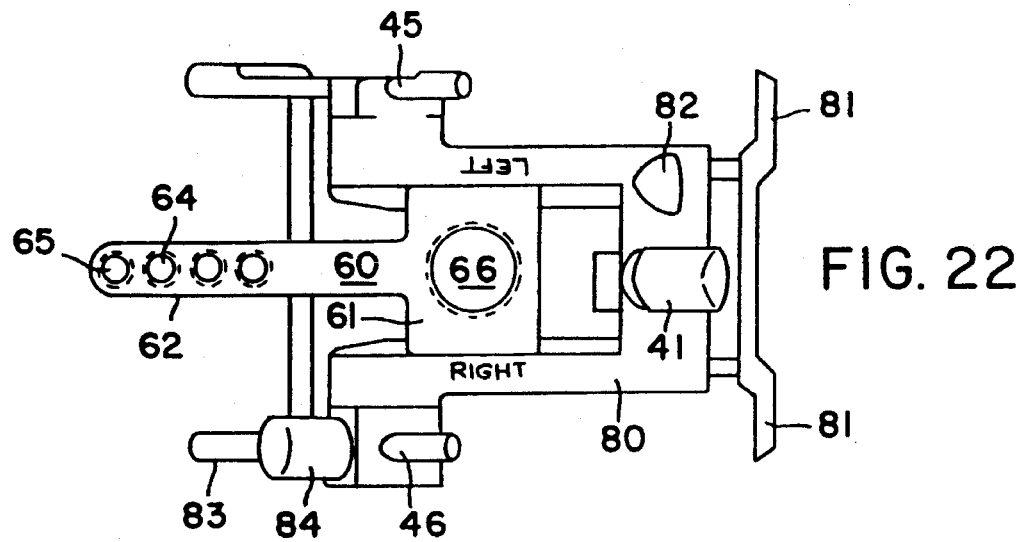
FIG. 22 is a plan view of the accessories shown in FIG. 21.

An anterior cortex/patella groove alignment accessory is shown in FIGS. 21 and 22 which allows anterior structures of the femur to be used to place the femoral component, the various parts described in the other figures being assembled together as shown.

Figure 23:
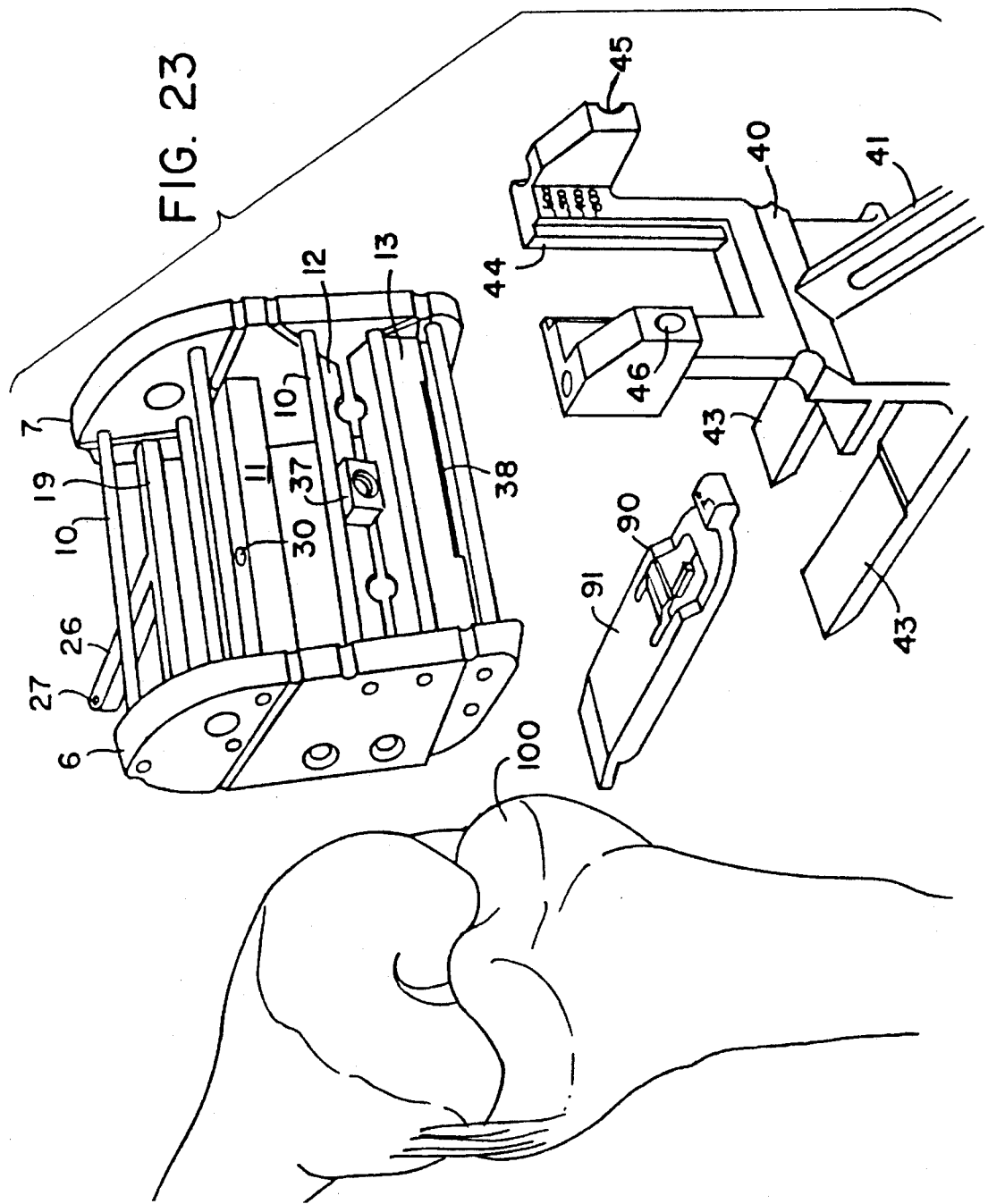
FIG. 23 shows an exploded assembly of the apparatus and including spacer blocks for application to the bone.
Figure 25:
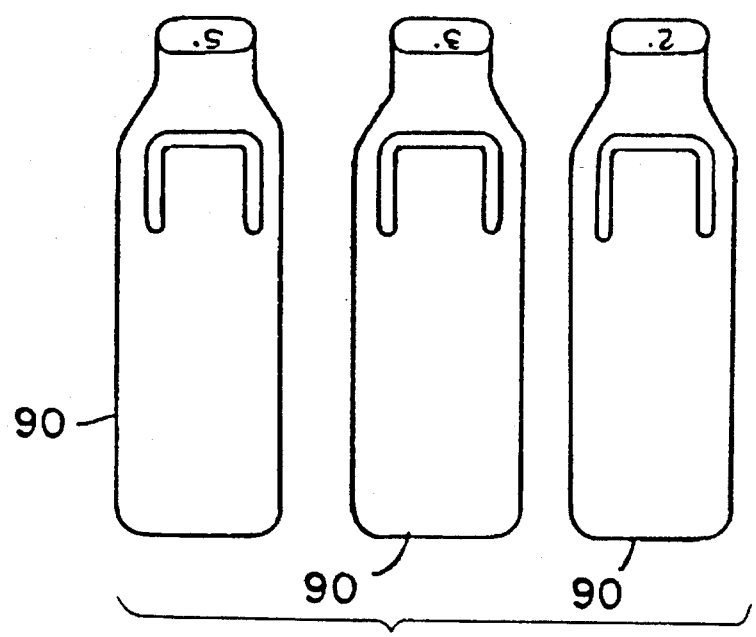
FIG. 25 is a plan view of three spacer blocks for use in the assembly as shown in FIG. 23.
Figure 24:
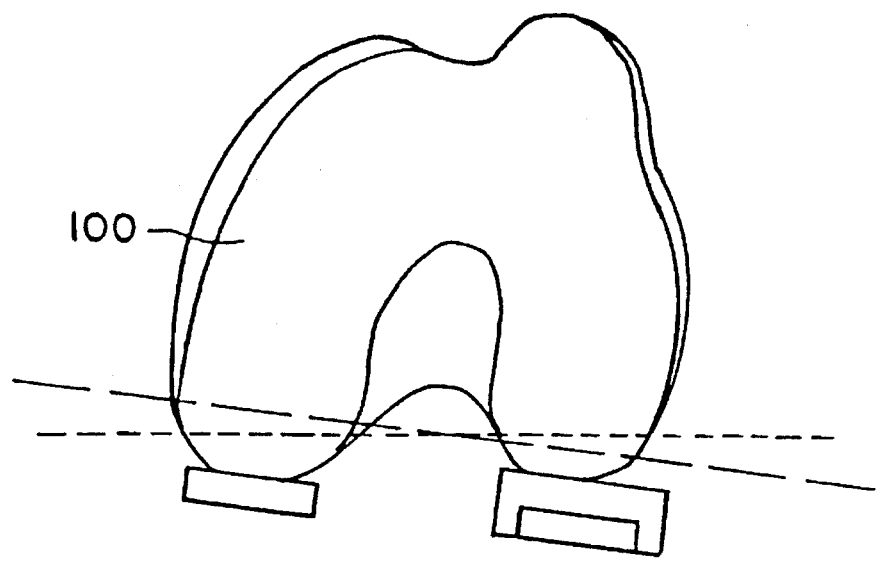
FIG. 24 is a diagrammatic view showing the use of spacer blocks.

The instruments described so far intend neutral alignment in internal-external rotation. According to the way that the proximal tibia is resected, it may be advantageous to externally rotate the femoral component relative to the natural anatomy. This is achieved by the construction shown in FIG. 23 in which spacer blocks 90 can be used which fit on to the arms 43 of accessory 40. FIG. 25 shows three blocks 90 which are marked as shown at 91 to show the degree of offset. FIG. 24 shows how the rotation is achieved. The bone in this figure and in FIG. 25 being indicated by reference numeral 100.

To use the instrument, the base component is initially assembled with the chosen femoral alignment accessory. In this case the technique will be described with respect to use of posterior condylar alignment accessory 40. The extramedullary alignment and drill guide 60 is then introduced into slide 44 on the alignment accessory so that pin 63 on the guide engages against the bottom face of counterbore 39 in cross bar 11 and a long alignment rod 65 is placed in a hole 64 so that the rod lies just above the skin on the patient's thigh and guide 60 is clamped by hand nut 69. The assembled instrument is then positioned so that alignment rod 65 passes over the center of the hip and is parallel to the femoral shaft in the sagittal plane. In cases of condylar bone loss, the condylar defect screws 31 are introduced and adjusted to stabilize the base component relative to the damaged distal femur.

With the instrument correctly aligned, sizing stylus 50 is introduced into posterior condylar alignment accessory 40 and pressed up against the anterior cortex. The size indication is then read from the scale marking 52. If the size reading does not correspond to the femoral guide currently in position, then the base component is replaced with one of the appropriate size. The procedure performed so far is then repeated. Sizing stylus 50 is removed. With the appropriately sized assembly correctly positioned extramedullary alignment and drill guide 60 is used to drill a pilot hole into the intercondylar area.

The extramedullary alignment and drill guide 60 is then removed and replaced with an intramedullary boss 75, appropriately oriented for the left or right limb and of a valgus angle setting determined from preoperative x-rays or surgeon preference. An intramedullary rod 77 is then introduced through the boss 75 until it engages into the isthmus of the femoral canal. The assembly consequentially repositioned relative to this new datum in its flexion extension and varus-valgus alignment. Anterior-posterior position is now reset by pressing the posterior condylar alignment accessory's skids 43 up against the posterior condyles. If intramedullary alignment is not possible or required, the preceding steps are omitted.

The positioned assembly is now pinned in place onto the distal femur using four pins passed through the holes 9 in the side plates 6, 7. These are introduced either by hammering, drilling or screwing, and may have heads to allow tensile capture of the jig. A hole is now drilled in the anterior cortex of the femur using the drill guide 27 on the anterior anchor 26 and the fixation pin 28 is inserted to stabilize the assembly.

All accessories are now removed from the base component. The cuts for the placement of the femoral component are now made using an oscillating saw. Preferably, these will be made in the following order: 1) anterior cut, 2) posterior cut, 3) posterior chamfer cut, 4) anterior chamfer cut, 5) distal cut.

The distal femur is resected last to allow the piece of bone which will be removed to support the guide while the other cuts are being made.

Where there is any doubt about the choice of component size, based on the stylus measurement and/or preoperative templating the largest of the possible sizes is chosen first. The anterior cut is made first to assure that the correct size is being used and this ensures that the initial anterior cut will not have removed bone needed for the fixation of a smaller sized component.

While several examples of the present invention have been described, it is obvious that many changes and modifications may be made thereunto, without departing from the spirit and scope of the invention.

I claim:

1. A femoral cutting guide for guiding system a cutting device for preparing the distal end of a human femur to receive an endoprosthetic femoral component comprising:

a base component including a pair of side walls;

a plurality of spaced apart guide rods extending between said side walls for guiding the cutting device for forming a distal femoral surface, an anterior femoral surface, a posterior femoral surface, and anterior and posterior chamfered femoral surfaces for receiving a femoral component;

an accessory removably attachable to one of said rods;

means for aligning said base component on the bone, including an intramedullary rod and an element having a generally circular hole for allowing the insertion of the intramedullary rod therethrough, said element removably attachable to said accessory, said hole adapted to be positioned adjacent the intercondylar notch of the distal femur when said element is attached to said accessory and said accessory is attached to one of said rods; and pin elements for attaching said base component to medial and lateral bone surfaces after alignment, said pin elements extending through holes in said side walls, said holes located proximally of said guide rods when said cutting guide is mounted on said femur.

2. The femoral cutting guide system as set forth in claim 1 further comprising an anterior anchor mounted on said base component to provide alignment said anterior anchor including means for anchoring said base component to the anterior cortex of the femur with which the instrument is to be used.

3. The femoral cutting guide system as set forth in claim 1 wherein said accessory is a posterior alignment accessory having a location means thereon which can locate against the posterior condyles of the bone and which acts as a condylar sled.

4. The femoral cutting guide system as set forth in claim 3 further including a sizing stylus wherein said posterior alignment accessory has means for attaching a sizing stylus.

5. The femoral cutting guide system as set forth in claim 4 wherein said sizing stylus and said posterior alignment accessory have cooperating indicators to indicate the appropriate femoral component size required.

6. The femoral cutting guide system as set forth in claim 3 including an extramedullary alignment guide removably attachable to said posterior alignment accessory and including means for orientating the guide system relative to the femoral geometry of the bone.

7. The femoral cutting guide system as set forth in claim 6 wherein said means for orientating is adapted to overlie the anterior surface of the femur to align to the femoral head from the center of the knee for varus-valgus alignment.

8. The femoral cutting guide system as set forth in claim 6 wherein said means for orientating provides extramedullary alignment by using the line of the anterior femoral shaft for varus-valgus orientation.

9. The femoral cutting guide system as set forth in claim 6 wherein a plurality of positions are provided for the orientating means.

10. The femoral cutting guide system as set forth in claim 6 wherein said extramedullary alignment guide incorporates means for guiding a drill for forming an entry hole in the intramedullary cavity to correspond with the intramedullary stem of a femoral implant component.

11. The femoral cutting guide system as set forth in claim 1 further comprising means to externally rotate a femoral component to be fitted relative to the natural anatomy of the femur and which includes means for rotating said base component relative to the bone.

12. The femoral cutting guides system as set forth in claim 1 wherein said guide rods are adapted to guide a saw blade.

13. A femoral cutting guide for guiding a saw blade for forming distal, posterior, anterior, anterior chamfer and posterior chamfer cuts on a distal femur to thus form a surface for mating with a prosthetic femoral component, the cutting guide comprising:

a pair of side plates;

a plurality of guide rods mounted to each side plate and extending therebetween to separate said plates, said guide rods mounted on said plates with respect to one another in a manner whereby five saw blade paths are defined, said distal cut in a direction transverse to a longitudinal axis of the femur, said anterior and posterior femoral cuts in directions parallel to said longitudinal axis and said anterior and posterior chamfer cuts at an angle to said longitudinal axis with at least one guide rod on each side of each cutting path, said guide rods of each side of said cutting paths spaced apart in a direction perpendicular to the cutting path a distance only slightly greater than a thickness of the saw blade so that said guide rods maintain the saw blades along said cutting path, means for aligning said base component on the bone, including an intramedullary rod and an element having a generally circular hole for allowing the insertion of the intramedullary rod therethrough said element attached to one of said guide rods, said generally circular hole adapted to be positioned adjacent the intercondylar notch of the distal femur; and a pair of generally circular holes for receiving pins in each of said side plates for mounting one of said pair of side plates to a medial side of the distal femur and the other plate to the lateral side of the distal femur, said holes located proximally of said rods when said cutting guide is mounted on the femur and angled towards said intramedullary rod.

14. A cutting guide for guiding a saw blade during the preparation of a distal femur for the implant of a femoral knee prosthesis, said cutting guide enabling guiding of said saw blade for cutting a distal face cut in a direction transverse to a longitudinal axis of the femur, an anterior femoral cut in a direction parallel to said longitudinal axis, an posterior femoral cut in a direction parallel to said longitudinal axis, an anterior chamfer and a posterior chamfer cut in a direction at an angle to said longitudinal axis of the femur, while said cutting guide remains located and secured to the femur in a single position on the distal femur, said cutting guide comprising:

a pair of side plates;

a first set of guide members extending laterally between said side plates and located to delineate transversely opposite boundaries of an axially directed anterior cutting path intercepting the anterior femur, said first set of guide members including opposite guide surfaces spaced apart axially along said anterior cutting path for guiding said saw blade along said anterior cutting path during the anterior femoral cut;

a second set of guide members spaced from said first set of guide members, said second set of guide members extending laterally between said side members and located to delineate transversely opposite boundaries of an axially directed posterior cutting path intercepting the posterior femur, said second set of guide members including opposite guide surfaces spaced axially along said posterior cutting path for guiding said saw blade along said posterior cutting path during the posterior femoral cut;

a third set of guide members extending laterally between said side members located to delineate opposite boundaries of a transversely directed distal cutting path intersecting the distal femur, said third set of guide members including opposite guide surfaces spaced apart axially along said transverse distal cutting path during the distal femoral cut; and a further set of guide members extending laterally between said side members and located for delineating transversely opposite boundaries of an oblique anterior chamfer cutting path and delineating transversely opposite boundaries of an oblique posterior chamfer cutting path, said further guide members including first opposite guide surfaces spaced apart along said oblique anterior chamfer cutting path for guiding said saw blade along said oblique anterior chamfer cut and second opposite guide surfaces spaced apart along said oblique posterior chamfer cutting path for guiding said saw blade during the posterior chamfer cut;

said side members being spaced apart laterally a distance sufficient to provide each of said delineated anterior cutting path, posterior cutting path, distal cutting path, anterior chamfer cutting path and posterior chamfer cutting path with a continuous, uninterrupted lateral extent corresponding to the full lateral extent of the respective transverse distal cut, anterior femoral cut, posterior femoral cut, anterior chamfer and posterior chamfer, whereby the full anterior femoral cut, the full posterior femoral cut, the full transverse distal cut, the full anterior chamfer and the full posterior chamfer cuts and accomplished while said cutting guide is located and secured on the femur in the single position;

means for aligning said base component on the bone, including an intramedullary rod and an element having a generally circular hole for allowing the insertion of the intramedullary rod therethrough mounted on one of said guide members, said hole adapted to be positioned adjacent the intercondylar notch of the distal femur; and a pair of generally circular holes for receiving pins in each of said side plates for mounting one of said pair of side plates to a medial side of the distal femur and the other plate to the lateral side of the distal femur, said holes located proximally of said guide members when said cutting guide is mounted on the femur.

* * * * *